United States Patent [19]

Boschetti

[11] 4,189,370
[45] Feb. 19, 1980

[54] PROCESS FOR OBTAINING GELS OF N-METHYLOL-ACRYLAMIDE COPOLYMERS AND APPLICATION OF SAID GELS FOR THE STEPPED GRADIENT SEPARATION OF SERIC LIPOPROTEINS

[75] Inventor: Egisto Boschetti, Chatou, France

[73] Assignee: Societe Sebia, Issy les Moulineaux, France

[21] Appl. No.: 917,549

[22] Filed: Jun. 21, 1978

[51] Int. Cl.² .................. G01N 27/26; G01N 27/28
[52] U.S. Cl. ......................... 204/299 R; 204/180 G; 210/31 C; 210/198 C
[58] Field of Search .............. 204/180 G, 299 R; 210/31 C, 198 C; 23/233 R, 233 TP, 111; 427/37

[56] References Cited

U.S. PATENT DOCUMENTS

| | | |
|---|---|---|
| 3,875,044 | 4/1975 | Renn et al. .................. 204/180 G X |
| 3,948,743 | 4/1976 | Monthony et al. ............. 204/180 G |
| 3,960,499 | 6/1976 | White ......................... 204/180 G X |
| 4,119,521 | 10/1978 | Chirikjian ................... 204/180 G X |

*Primary Examiner*—Arthur C. Prescott
*Attorney, Agent, or Firm*—Gifford, Chandler, VanOphem, Sheridan & Sprinkle

[57] ABSTRACT

A process for preparing plates of a new gel polymer, said plates being adapted to the electrophoresis separation of the seric or plasmatic lipoproteins under a stepped gradient. The gel polymers are prepared by radical polymerization of N-methylol-acrylamide and of a bifunctional allylic or acrylic compound causing cross-linking to yield a tridimensional configuration polymer. The polymerization may optionally be catalyzed by peroxides and/or ultraviolet radiation. Anionic polysaccharides containing only COOH groups may be added to assist migration of lipoproteins in the gel.

20 Claims, No Drawings

PROCESS FOR OBTAINING GELS OF N-METHYLOL-ACRYLAMIDE COPOLYMERS AND APPLICATION OF SAID GELS FOR THE STEPPED GRADIENT SEPARATION OF SERIC LIPOPROTEINS

BACKGROUND OF THE INVENTION

Field of the Invention

This invention relates to a process for preparing plates comprising a new gel polymer used alone or combined with other polysaccharides such as agar or agarose, said plates being adapted to the electrophoresis separation of the seric or plasmatic lipoproteins under a stepped gradient. Such gel polymer is fixed upon a transparent polyester film used as a mechanical support. The invention also relates to the dried and rehydratable plates obtained by this process.

It is known that the separation of human lipoproteins is carried out upon natural supports such as agar, agarose, or gelled starch, or synthetic supports such as cellulose acetate or gelled acrylamide.

In the case of supports made of agar, agarose and cellulose acetate, the electrophoretic separation shows four characteristic fractions named according to their increasing mobility: beta-lipoproteins, pre-beta-lipoproteins, alpha-lipoproteins and pre-alpha-lipoproteins.

When, in pathologic conditions there are, in the serum, micella of fatty compounds said chylomicrons, the electrophoresis normally shows a more or less noticeable trace at the beginning of the migration, said trace being revealed through liposoluble colouring reactants. In most cases however, the mechanism is more complicated. In view of their variable size, the chylomicrons are fractionated into three groups a first group localized on a line (or trace) at the starting line, a group spread between the starting line and the beta fraction and a group of a mobility substantially equal to the pre-beta-lipoproteins. The amount of said three forms differs depending on the case and above all on the support used in the electrophoresis. It is clear that such a picture is not representative of the reality, and this makes interpretation difficult, and leads to important analytical errors.

In the case of the classical supports of acrylamide and starch gel, the difficulty lies in the migration of the beta and pre-beta-lipoproteins. In fact, due to the very small size of the pores of the gel, such molecules cannot move. Attempts have been made to make possible the migration of the lipoproteins in a discontinuous gel of polyacrylamide, by decreasing to the extreme the polymer concentration. Such gels which are too soft to be handled are cast inside a small glass tube in which the electrophoretic migration is carried out. Despite rather good results, the interpretation remains difficult in view of the fact that it is impossible to obtain an accurate quantitative measure of each colored fraction by a densitometric method.

SUMMARY OF THE INVENTION

The plates of this invention obviate those drawbacks. The chilomicrons are totally stopped at the starting tank, the pre-beta-lipoproteins are stopped at the discontinuous gradient, and the beta, alpha and pre-alpha-lipoproteins are fractionated through their difference of mobility in the more concentrated area of the gel-polymer. The densitometric reading of such a picture no longer suffers from the drawback of the cylinders and finally it is possible to air-dry the plate after use to obtain then a transparent and flexible film easy to stock.

The plate is made of a transparent polyester support upon one face is stratified the gel-polymer. The face of said plastic support receiving the gel is pretreated by the usual procedures making it wettable. The gel-polymer is divided into two areas of different concentrations, the first taking about ⅔ of the available area. The separation line of two gels of the same kind but of different concentrations is rectilinear.

The gel-polymer is obtained by radical polymerisation of N-methylol-acrylamide and of a bifunctional allylic or acrylic compound causing the cross-linking, i.e. the tridimensional configuration of the polymer. Said polymerisation can be catalyzed by peroxides and/or under U.V. radiation.

According to a feature of the invention, it has been found that it can be added to assist the migration, anionic polysaccharides containing only COOH groups such as, for example, the strong endosmatic agarose AGAROSE HEEO (Marine Colloids Inc., Rockland, Maine, USA).

The process of the invention comprises (a) preparing two hot aqueous or buffered solutions strongly endosmotic polysaccharide each containing the requested elements for the polymer; (b) casting each solution at a well fixed moment in a plastic mold containing the polyester film; (c) cooling and withdrawing the gel from the mold, then washing it in an isotonic solution; (d) recovering the buffered gel, of given thickness and shape, fixed upon the polyester film. Such product, a "lipofilm", can be kept at 4° C. in any closed container, such as a plastic box or a polyethylene or aluminum sealed bag.

The monomer concentrations are: 2.5 and 7.5% of cross-linking ratio for the first layer and 2.0 and 10–17% of cross-linking ratio for the second layer. The polysaccharide concentrations can vary between 0.1 and 1%.

As catalytic systems, there can be used, for example:
NNN'N'-tetramethylethylenediamine-ammonium persulfate
NNN'N'-tetramethylethylenediamine-riboflavine-hydrogen peroxide-U.V.

The bifunctional allylic or acrylic compounds used as cross-linking agents can vary according to the requested solubility of the gel. Such a characteristic is determined by the process selected for the quantitative evaluation of the lipoprotein fractions:
an insoluble gel is requested for a densitometric study
a gel soluble in proper chemical solvents is requested for a study through elution.

As examples it can be cited:
NN'-methylene bis-acrylamide leads to an insoluble gel
Diallyltartramide leads to a gel soluble in 2% periodic acid
Ethylenediacrylate leads to gels soluble in basic media.

According to a further feature of the invention the plates of gel-polymers can also be treated to be dehydrated and rehydratable through simple chemical processes. Actually it has been found that if the gel is washed in a solution prepared from a mixture of a simple sugar, a diol or a triol and a carboxylic polysaccharide, previously treated by a reducing agent, such a washed gel can be air-dried, then regain its original characteristic through rehydratation in distilled water.

A simple sugar can be for example sorbitol used at a 10% or less concentration. A carboxylic polysaccharide can be for example purified sodium or ammonium alginates or soluble sodium carboxymethylcellulose. Such products are characterized by a complete solubility in aqueous medium and by a viscosity less than 30 cp (1.2% aqueous solution at 20° C.). Their concentration in the washing solution is at most 0.5%. The diol and the triol can be respectively ethylene glycol and glycerol used at a 1% concentration. The reducing agents can be inorganic salts such as sodium or potassium borohydrides, or aluminium-lithium hydride, used at a 0.02% concentration. The reduction should be carried out when the compounds are well dissolved in water, and it starts as soon as the reducing agent is added, as shown by more or less of a release of native hydrogen.

DESCRIPTION OF THE PREFERRED EMBODIMENT

The invention will now be illustrated by the following noliminting examples.

EXAMPLE 1

There is prepared a buffered trisglycine solution comprising 6 g/l of tris-hydroxymethylaminomethane and 28.8 g/l of glycine. In a first Erlenmeyer containing 40 ml of said buffer solution is added 1.66 ml of a 60% aqueous solution of hydroxymethylacrylamide and 78 mg of N,N'-methylene-bis-acrylamide. In a second Erlenmeyer containing 20 ml of said buffer solution is added 0.66 ml of a 60% aqueous solution of N-methylolacrylamide and 52 mg of N,N'-methylene-bis-acrylamide. Both Erlenmeyer are kept in a water bath at 45° C. To the first one is added 0.02 ml of NNN'N'-tetramethyl-ethylenediamine and 0.53 ml of a 100 mg/ml ammonium persulfate aqueous solution. The solution contained in this first Erlenmeyer is immediately injection cast in the mold until the requested level. After 45 minutes, the polymerization is complete. In the second Erlenmeyer is added 0.01 ml of NNN'N'-tetramethylethylmediamine and 0.1 ml of a 100 mg/ml ammonium persulfate aqueous solution, and the contents of this second Erlenmeyer is cast in the mold containing the first polymerized solution. After completion of the polymerization, the gel can be used directly in the mold.

EXAMPLE 2

In a first Erlenmeyer containing 40 ml of distilled or demineralized water is added 200 mg agarose HEEO, and dissolved by warming. In a second Erlenmeyer containing 20 ml of distilled water is added and dissolved in the same manner 100 mg of agarose HEEO.

Then the procedure of Example 1 is repeated except that the gel obtained after polymerization and cooling is withdrawn from the mold and washed in the buffer tris-glycine solution of Example 1. After washing the gel can be kept at 4° C. in a sealed bag.

EXAMPLE 3

The process of Example 2 is repeated except that the mold comprises a first face made of an hydrophilic polyester sheet previously activated, serving as support, and a second face made of an hydrophobic plastic material. The obtained gel can be kept for a prolonged period if protected from the heat in a waterproof bag.

EXAMPLE 4

The process of Example 3 is repeated, except that the catalist system NNN'N'-tetramethylethylenediamine/Riboflavine/hydrogen peroxyde/UV-irradiation is substituted to the catalyst system NNN'N'-tetramethyle-thylenediamine-ammonium persulfate. The amounts of the chemicals are:

| COMPOUNDS | FIRST LAYER (ml) | SECOND LAYER (ml) |
| --- | --- | --- |
| NNN'N'-tetramethyl-ethylenediamine | 0.02 | 0.01 |
| Riboflavine (0.0865% aqueous solution) | 0.26 | 0.13 |
| Hydrogen Peroxide (3%) | 0.028 | 0.014 |
| UV Irradiation | 30–60 minutes | 60 minutes |

After washing the gel with a proper buffer, the lipofilm can be immediately used, or kept at 4° C. in a sealed plastic bag.

EXAMPLE 5

The process of Example 3 is repeated except that an equivalent amount of diallyltartramide is used in place of NN'-methylene-bis-acrylamide. The obtained gel possesses the same characteristics but can be solubilized in a 2% solution of periodic acid, which enables elution of the lipoproteic fractions, in view of a spectrophotometric study upon the remaining solution, or in any further study.

EXAMPLE 6

The process of Example 5 is repeated except that an equivalent amount of ethylenediacrylate is substituted to diallyltartramide. The obtained gel possesses the same characteristics, but can be solubilized in an alkali solution, which enables elution of the lipoproteic fraction, in view of a spectrophotometric study upon the remaining solution, or in any further study.

EXAMPLES 7–7'

The process of Example 4 is repeated, except that equivalent amounts of diallyltartramide and of ethylene-diacrylate are used instead of NN'-methylene-bis-acrylamide.

The gel obtained by photochemical polymerization under UV irradiation, after withdrawal from the mold and washing can be used as described in Examples 5 and 6.

EXAMPLE 8

The process of Example 3 is repeated except that, for the washing solution (tris-glycine buffer) there is substituted a solution enabling the gel to be rehydratable after washing.

The procedure is as follows: Under magnetic stirring, 10 g (D)-Sorbitol, 1 ml ethyleneglycol and 0.2 g purified sodium alginate (of 20 cp viscosity in 1.2% solution at 20° C.) are dissolved in an Erlenmeyer, containing 95 ml of distilled or demineralized water. After complete dissolution, 20 mg of sodium borohydride are added. The stirring is maintained until the end of gaseous evolving. The obtained solution is poured in a tank equipped with a horizontal stirrer, and the gel is immersed into the solution. After at least 12 hours of washing, the gel is air dried. There is thus obtained a flexible and transparent gel which can be completely rehydrated within 2 hours in a bath of demineralized water. The rehydrated gel possesses all the characteristics of the gels of Examples 1 to 7.

EXAMPLE 9

The process of Example 8 is repeated except that an equivalent amount of sodium carboxymethylcellulose is used as washing solution instead of the sodium alginate, the viscosity characteristics remaining the same.

The obtained film after air-drying possesses all the characteristics of a rehydratable gel without changing of any of its original characteristics.

What I claim is:

1. A process for preparing gels stratified upon a film, said gels being adapted for electrophoretic separation of seric and plasmatic lipoproteins, said gel further being a high polymer of N-Methylol-Acrylamide, said process comprising the steps of:
   (a) disposing upon said film a first gel comprising a high polymer of N-Methylol-Acrylamide, said first gel being formed from a first monomer concentration; and
   (b) disposing upon said film a second gel comprising a high polymer of N-Methylol-Acrylamide said second gel being formed from a second monomer concentration different than said first monomer concentration, so as to form a discontinuous gradient between said first gel and said second gel; whereby electrophoretic separation of seric and plasmatic lipoproteins is enhanced by said discontinuous gradient.

2. A process according to claim 1, wherein said high polymer of N-Methylol-acrylamide is further formed from a jellifiable polysaccharide containing carboxyllic groups.

3. Process according to claim 1 said high polymer is obtained through copolymerizing N-methylolacrylamide with a bifunctional allylic or acrylic compound.

4. Process according to claim 3, wherein, to obtain an insoluble gel, said bifunctional compound is NN'-methylene-bis-acrylamide.

5. Process according to claim 3, wherein to obtain a gel soluble in a 2% aqeuous solution of periodic acid, said bifunctional compound is diallyltartramide.

6. Process according to claim 3, wherein to obtain a gel soluble in alkali solutions, said bifunctional compound is ethylene-diacrylate.

7. Process according to claim 1, wherein said first gel forms a first layer and said second gel forms a second layer spaced from said polyester film and disposed on said first layer.

8. Process according to claim 3, wherein said first monomer concentration is about 2.5%, said second monomer concentration is about 2%, the concentration of said bifunctional allylic or acrylic compound is about 7.5% for said first gel, and the concentration of said bifunctional allylic or acrylic compounds is about 10–17% for said second gel.

9. Process according to claim 2, wherein said polysaccharide is a gel of strongly electro endosmatic agarose containing only carboxylic groups.

10. Process according to claim 9, wherein the concentration of said polysaccharide is 0.1 to 1%.

11. Process according to claim 1, wherein said film used as support comprises an activated hydrophobic face.

12. Process according to claim 1, wherein said first gel and said second gel further contain agents enabling the rehydration of the dried gel.

13. Process according to claim 12, wherein said agents are previously treated, then included by washing into said first gel and said second gel.

14. Process according to claim 13, wherein said agents are polysaccharides of low molecular weight having a viscosity less than 30 cp in a 1.2% solution at 20° C.

15. Process according to claim 14, wherein said polysaccharides are negatively charged through carboxylic groups under the form of sodium or ammonium salts.

16. Process according to claim 12, wherein said agents are a member selected from the group consisting of sorbitol, ethylene glycol, and glycerol, used at a concentration of 1–10%.

17. Process according to claim 13, wherein said treatment is a reduction.

18. Process according to claim 17, wherein said reduction is carried out through inorganic hydrides.

19. Process according to claim 16, wherein said hydrides are a member selected from the group consisting of sodium borohydride, potassium borohydride, and aluminum-lithium hydride.

20. A plate adapted for electrophoretic separation of seric and plasmatic lipoproteins, said plate comprising:
   a film suitable for support of electrophoresis gels;
   a first gel disposed upon said film, said first gel comprising a high polymer of N-Methylol-Acrylamide, said first gel being formed from a first monomer concentration; and
   a second gel disposed upon said film so as to form a separation line between said first gel and said second gel, said second gel comprising a high polymer of N-Methylol-Acrylamide, said second gel being formed from a second monomer concentration different than said first monomer concentration, whereby electrophoretic separation of seric and plasmatic lipoproteins is enhanced by said separation line.

* * * * *